United States Patent
Ansari

(10) Patent No.: US 11,077,230 B2
(45) Date of Patent: Aug. 3, 2021

(54) DECELLULARISING TISSUE

(71) Applicant: VIDEREGEN LIMITED, Liverpool (GB)

(72) Inventor: Tahera Ansari, Harrow (GB)

(73) Assignee: VIDEREGEN LIMITED, Liverpool (GB)

( * ) Notice: Subject to any disclaimer, the term of this patent is extended or adjusted under 35 U.S.C. 154(b) by 183 days.

(21) Appl. No.: 15/769,004

(22) PCT Filed: Oct. 18, 2016

(86) PCT No.: PCT/GB2016/053231
§ 371 (c)(1),
(2) Date: Apr. 17, 2018

(87) PCT Pub. No.: WO2017/068336
PCT Pub. Date: Apr. 27, 2017

(65) Prior Publication Data
US 2018/0311409 A1    Nov. 1, 2018

(30) Foreign Application Priority Data
Oct. 21, 2015  (GB) .................................... 1518657

(51) Int. Cl.
*A61L 27/36*    (2006.01)

(52) U.S. Cl.
CPC ....... *A61L 27/3683* (2013.01); *A61L 27/3633* (2013.01); *A61L 2430/40* (2013.01)

(58) Field of Classification Search
CPC ............. A61L 2430/40; A61L 27/3683; A61L 27/3633; A61L 27/3687; A61L 27/3691; A61L 27/3695; A61F 2/04
See application file for complete search history.

(56) References Cited

U.S. PATENT DOCUMENTS

| | | | |
|---|---|---|---|
| 2010/0323440 A1 | 12/2010 | Ngo et al. | |
| 2011/0165676 A1* | 7/2011 | Hopkins | .................. C12N 1/08 435/378 |
| 2012/0302499 A1 | 11/2012 | Matheny | |

OTHER PUBLICATIONS

K. Sawada et al: "Cell removal with supercritical carbon dioxide for acellular artificial tissue", Journal of Chemical Technology & Biotechnology, vol. 83, No. 6, Jun. 1, 2008 (Jun. 1, 2008), pp. 943-949.
Heck, Georg, International Search Report, European Patent Office dated Jan. 25, 2017.
Crapo et al., "An overview of tissue and whole organ decellularization processes," Biomaterials 32 (2011) 3233-3243.

* cited by examiner

*Primary Examiner* — Blaine Lankford
(74) *Attorney, Agent, or Firm* — Florek & Endres PLLC

(57) ABSTRACT

The invention provides a method for decellularising a tissue the method comprising the steps of: a) adding a tissue to be decellularised to a decellularisation vessel; b) adding a decellularisation medium comprising at least one detergent and/or at least one enzyme to the vessel; c) introducing a supercritical fluid to the vessel; and d) maintaining contact of the tissue with the supercritical fluid for a time sufficient to substantially decellularise the tissue.

14 Claims, 1 Drawing Sheet

DECELLULARISING TISSUE

TECHNICAL FIELD OF THE INVENTION

This invention relates to methods of decellularising tissue, in particular using supercritical fluid and a decellularisation medium. The invention further relates to methods of manufacturing decellularised implants and to implants per se.

BACKGROUND TO THE INVENTION

Many patients with chronic conditions requiring tissue replacement or repair or organ transplantation endure a poor quality of life on expensive chronic care regimes. The field of regenerative medicine holds immense potential for improving the quality of life of patients with diseased or injured tissues/organs. It offers significant potential and opportunities for the treatment of these conditions and to address unmet clinical and patient needs which will have a major impact on clinical outcomes in the coming years. By 2013 tissue engineering and regenerative medicine is estimated to have a global market potential in excess of $118 billion. However, this potential is generally centred on translational research outcomes reaching patients in a timely manner. There is a continuing and increasing demand for new solutions for the replacement of diseased or injured tissue. Conventional tissue replacement or organ transplantation is not always suitable and there is insufficient tissue or organ availability and a lack of synthetic alternatives.

The technology behind creating simple biological scaffolds has been in place for a number of years but has not evolved beyond simple washing and perfusion steps. The overall process is both labour and time expensive and there has generally not been any implementation of complex implant structures and "off the shelf products". The majority of biological scaffolds are produced by de-cellularising cadaveric tissue; this process removes all immunogenic cells and debris leaving behind an acellular piece of tissue composed of collagen, elastin and surface proteins. Known processes either wash or perfuse tissues with aggressive and damaging de-cellularising reagents. For dense tissue with a limited vascular supply, (e.g. cartilage, bone or tendon), under current processes, penetration of the reagents deep into the tissue is also time-consuming and problematic. The ideal scenario would deliver the de-cellularising reagents into tissues as a gas and remove the debris dissolved in a liquid.

Carbon dioxide ($CO_2$), when compressed and heated, enters a supercritical phase (SC) where it simultaneously exhibits both gaseous and fluid properties. In order to achieve this, it must reach its critical point (Tc=31.1° C. and Pc=7.38 MPa); changing the temperature and pressure changes the phase from solid to liquid to gas. However, at the critical point (the intersection of $T_c$ and $P_c$), the distinction between the liquid and gas phases disappear. The single fluid phase $CO_2$ at this point is said to be supercritical. An attractive feature of SC—$CO_2$ is its transport coefficient. The diffusion coefficient of SC—$CO_2$ is intermediate between liquid and gas but the viscosity is similar to gases. Since the viscosity is that of a gas, a supercritical fluid has high transfer rate and high permeability, both of which can be manipulated by altering the temperature and pressure. $CO_2$ is the most frequently used solvent since it is safe, non-toxic, non-corrosive, inflammable, readily available and cheap. It is used extensively in the pharmaceutical industry for the processing of thermo-sensitive and bioactive compounds. Within the tissue engineering field it is predominantly used to create synthetic polymers and scaffolds. The moderate pressure and temperature required to reach its critical point and become a supercritical fluid are easily achievable and compatible with biological tissue and unlikely to impact on the mechanical properties of the tissue. Additionally, any $CO_2$ remaining in the tissue after the supercritical phase will return to its gaseous phase and diffuse out of the tissue.

SC—$CO_2$ has been used to de-cellularise tissue. In the first study by Frayssinet et al., 1998 Biomaterials 19:2247-2253 it was used to produce allogeneic pieces of cancellous bone and was used to remodel bone in an in vivo sheep model. Additionally this group also used SC—$CO_2$ to inactivate human viruses: HIV-1, Sindbis, virus, Polio sabin type 1 and Pseudorabtes (PRV). A later study by Sawada et al., 2008 J of chemical tech and biotech 83: 943-949 used SC—$CO_2$ together with ethanol to produce acellular porcine aorta. SC—CO together with peracetic acid has also been used to inactivate bacterial spores and viruses in acellular dermal matrix. In each case the use of harsh solvents creates an environment in which the tissue may be damaged, and use of such solvents may not fully decellularise the tissue.

U.S. Pat. No. 8,974,730B2 also describes the use of supercritical $CO_2$ to decellularise soft tissue, in which contaminants of the tissue, such as cells and cell debris are removed by extracting them in supercritical $CO_2$ and rapidly depressurising the vessel in which the decellularisation is performed. The use of a supercritical fluid alone, such as $CO_2$, followed by rapid depressurisation does not fully decellularised the tissue, and the process may damage or destroy the underlying collagenous extracellular matrix (ECM) architecture and substructure.

It would therefore be advantageous to provide a method of decellularising tissue, and manufacturing tissue implants, in which supercritical fluids, such as $CO_2$, are utilised, but which overcome or mitigate the issue of the prior art methods, such as incomplete decellularisation or damage to the retained ECM of the resultant tissue scaffold.

It is therefore an aim of embodiments of the invention to overcome or mitigate at least one problem of the prior art, as described hereinabove, or otherwise described.

SUMMARY OF THE INVENTION

According to a first aspect of the invention there is provided a method for decellularising a tissue, the method comprising the steps of:
a) adding a tissue to be decellularised to a decellularisation vessel;
b) adding a decellularisation medium comprising at least one detergent and/or at least one enzyme to the vessel;
c) introducing a supercritical fluid to the vessel; and
d) maintaining contact of the tissue with the supercritical fluid for a time period sufficient to substantially decellularise the tissue.

The supercritical fluid may be supercritical carbon dioxide.

Steps a) and b) may be in any order.

Cell nuclei are highly polar and do not generally dissolve in non-polar $CO_2$, whereas non-polar components of cells like hydrocarbons and oils readily dissolve. Conversely, polar molecules in cells, such as amino acids and proteins, are less readily soluble. The action of $CO_2$ on the cells of a tissue is believed to encompass one or more of the following effects: cell membrane modification, decrease in intracellular pH; inhibiting effect at $CO_2$ and $HCO_3$ on metabolism; disordering of intracellular electrolyte balance; and removal of vital constituents from cells and cell membranes. Thus the use of $CO_2$ is believed to ensure maximum degradation of cells and cellular matter, enabling removal of the cells and cellular matter more easily, to leave the extracellular matrix of the cell intact. In addition the disruption of the cells and cell membranes enables the detergent and/or enzyme from step b) of the method to be delivered to the tissue more effectively and to perfuse further and faster into the tissue, for optimising decellularisation. Finally, the $CO_2$, due to its cell disruption properties, enables effective anti-microbial action in relation to any microbes present on or in the tissue.

The detergent may comprise sodium dodecyl sulphate (SDS), sodium deoxycholate (SOC), a detergent comprising hydrophilic polyoxyethylene-oxide and hydrophilic hydrocarbon moieties (such as Triton X-100®), or any combination thereof. In some embodiments the detergent comprises a mixture of SDS and SOC, SDS and a detergent comprising hydrophilic polyoxyethylene-oxide and hydrophilic hydrocarbon moieties, SOC and a detergent comprising hydrophilic polyoxyethylene-oxide and hydrophilic hydrocarbon moieties, or SDS, SOC and a detergent comprising hydrophilic polyoxyethylene-oxide and hydrophilic hydrocarbon moieties.

The enzyme may comprise a proteolytic enzyme, a lipase, a cellulase, a nuclease, or any combination thereof. In some embodiments the proteolytic enzyme comprises trypsin. In some embodiments the nuclease comprises a deoxyribonuclease such as DNase I or a ribonuclease such as RNase or a combination thereof. In some embodiments the enzyme comprises a proteolytic enzyme and a nuclease, which may comprise trypsin and one or both of a deoxyribonuclease and ribonuclease.

In some embodiments step b) comprises adding a decellularisation medium comprising both a detergent and an enzyme. The decellularisation medium may comprise a detergent selected from SDS, SOC and a detergent comprising hydrophilic polyoxyethylene-oxide and hydrophilic hydrocarbon moieties, and an enzyme selected from a proteolytic enzyme, a nuclease, a lipase and a cellulase.

In some embodiment the decellularisation medium comprises SDS, and/or SOC and trypsin and/or a nuclease (which may be a DNase or RNase).

The method may comprise agitating and/or stirring the mixture in the vessel during any or all of steps b), c) and d).

The vessel may be heated to a temperature of at least 28° C., 29° C., 30° C., 31° C., 32° C., 33° C., 34° C. or 35° C. during any or all of steps a) to d) and in some embodiments is heated to around 31° C. to 35° C. during at least steps c) and d) or at lease steps b), c) and d) or all of steps a) to d).

The supercritical fluid may be supercritical $CO_2$ (carbon dioxide) which is introduced into the vessel at a pressure of at least 8 MPa, at least 10 MPa, at least 20 MPa, at least 50 MPa, at least 100 MPa or at least 125 MPa. In some embodiments the supercritical $CO_2$ may be at a pressure of 150 MPa or more.

The supercritical fluid may be added to the vessel at a rate of at least 0.1 ml/minute, 0.2 ml/minute, 0.5 ml/minute or 1.0 ml/minute and the flow rate may be constant or may be varied over time.

The decellularisation medium may have a pH of between 5 and 8, or between 6 and 7.5. The tissue may be maintained in contact with the decellularisation medium for at least 12 hrs, 18 hrs, 24 hrs, 30 hrs or 36 hrs. The tissue may be maintained in contact with the decellularisation medium for between 24 hrs and 48 hrs, or between 30 hrs and 48 hrs.

After step d) there may be a further step e) of washing the decellularised tissue. Washing may comprise contacting the tissue with a washing buffer, such as phosphate buffered saline (PBS). Washing may be performed for up to 12 hrs, 18 hrs, 24 hrs, 30 hrs, 36 hrs or 48 hrs, and may comprise changing the washing buffer at defined time intervals, such as every 6, 8 or 12 hrs, for example.

The tissue may be selected from endothelial tissue, epithelial tissue, interstitial tissue, connective tissue, or supporting tissue. The tissue may be trachea, oesophagus, larynx, bowel, intestine, vascular tissue, bone, ligament, tendon, urethra, bladder, skin, lung, muscle, buccal tissue, pancreas, spleen, kidney, liver, lymphatic, brain, bone-tendon, bone-ligament, synovial membrane, cartilage per se and nervous tissue.

When cartilaginous tissue is used, the method of the invention results in decellularisation of the tissue such that substantially all chondrocytes within the lacunae are removed. In addition, when the tissue is trachea, substantially all of the nuclei within the luminal epithelium (mucosa), submucosal glands, trachealis muscle and outer adventitia are removed.

After decellularisation, the remaining scaffold comprises extracellular matrix ("ECM"), in particular collagen. The structure of the ECM is at least partially, and may be fully, preserved in the scaffold. Thus the collagen scaffold remaining may comprise collagen fibres displaying original architecture and molecular ultrastructure of the natural tissue material from which it is desired. The natural three-dimensional structures of the fibrous tissue proteins are preferably substantially retained, through some loosening or unfolding is acceptable, without significantly affecting the structural integrity of the scaffold.

It is known that cellular components specific for the scaffold's origin and/or the place of its implantation will invoke proper constructive remodelling of the ECM only when the polymeric architecture of the fibres within the decellularised tissues or organs remains at least partially intact. Therefore, ECM is better suited than any synthetic matrix to elicit functional regenerative remodelling, and provide a successful scaffold for tissue growth.

Preservation of functional ECM proteins is also important for maintenance of the biological activity, structural integrity, durability and physic-chemical properties of the scaffold. Maintenance and preservation of the hierarchy of structure from the molecular structure of proteins and glycosaminoglycans (GAGs) through to macroscopic ultrastructure of the tissue is important for the inherent physicomechanical properties with in turn are important for tissue function. Preservation of the three-dimensional structures during decellularisation and tissue processing also improves the ultimate cellular repopulation of the tissue and regeneration of cellular and tissue-specific function.

The present invention preferably preserves ECM-derived and located GAGs while substantially removing cell-associated GAGs. Thus the process of decellularisation generally results in a reduction of total GAGs, while the ECM-associated GAGs are preferably largely preserved. This is important, as there is "cross-talk" between ECM GAGs and different cell types, helping to direct cell trafficking and cell differentiation. The ECM GAGs also serve as a store or sink for growth factors, which helps to direct tissue regeneration after implantation of the scaffold/implant.

The method may comprise a method of manufacturing a tissue implant or tissue scaffold.

According to a second aspect of the invention there is provided a tissue implant or scaffold manufactured using the method of the first aspect of the invention.

DESCRIPTION OF THE INVENTION

The various aspects of the invention will now be described by way of example, with reference to the accompanying Figures, in which.

EXAMPLES

Example 1

Test Material

Porcine tissue was harvested and stored dry at −20° C. until required; the tissue comprising samples of trachea, tendon, bone and aorta and oesophagus.

$SC-CO_2$ Set-Up

Optimised de-cellularisation for tracheal tissue was carried out using a high pressure reaction system. The system consisted of a pressurising $CO_2$ pump (PU2080-$CO_2$ SFC/SFE pump with peltier cooled head-Jasco UK), A cylinder of liquid $CO_2$, a 50 ml stainless steel vessel customised to receive a temperature probe, a back pressure regulator (BP-2080-81 Automatic back pressure regulator—Jasco UK and an column oven (Co-960 column oven). A teflon coated bar and a magnetic stirrer were used to agitate the solution within the vessel.

Tissue De-Cellularisation

Each piece of tracheal tissue (n=4 samples, T1 to T4) was weighed and its length recorded. 25 ml of a decellularisation medium comprising 0.25% Triton x-100, 0.25% SOC, 100 µg/ml RNase, 400 KU of DNase in DMEM and 25 ml of a phosphate buffered saline (PBS) wash was added into the vessel and the tissue placed into the vessel. The vessel was placed in the column oven set at the required temperature (37° C.), (temperature inside the vessel was also initially measured at 36.8° C.). Supercritical $CO_2$ was pumped into the vessel using the pressurised $CO_2$ pump at a constant flow rate (1 ml/minute) until a pressure of 150 MPa was reached. The system was then maintained at constant pressure using the constant pressure/constant flow feature on the $CO_2$ pump. At the end of each experiment the vessel was depressurised over a 15 minute period at a constant sequential drop in pressure. Each experiment was run over a 36-48 hour period with cyclical changes, in approximately 12 hr intervals, of the decellularisation medium and wash buffer.

Analysis

Figure 1:
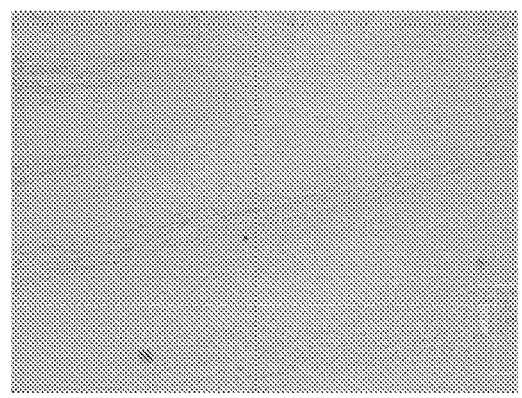
FIG. 1 is a histological micrograph of a decellularised tissue prepared by the method of Example 1.
Figure 2:
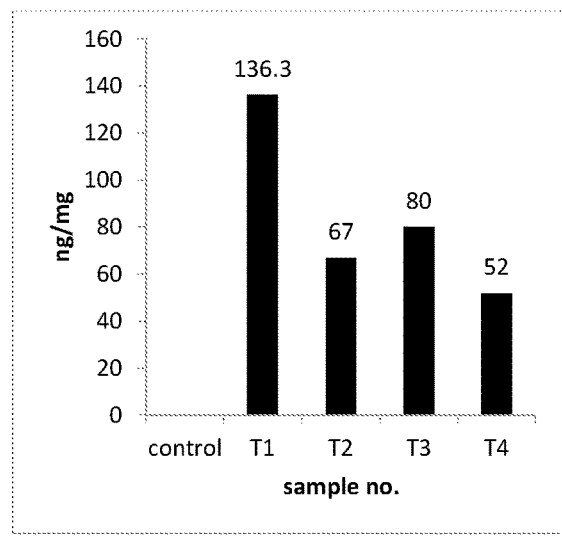
FIG. 2 is a graph illustrating the concentration of DNA present in tissue samples prepared using the method of Example 1.
Figure 3:
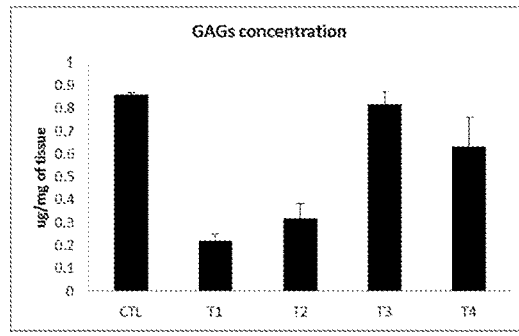
FIG. 3 is a graph illustrating the concentration of GAGs (glycosaminoglycans) present in tissue samples prepared using the method of Example 1.

Following completion of each experiment the tissue was fixed in 10% neutral buffered formal saline, processed for wax embedding and 5 µm sections cut and stained with H&E and Picro-sirius red with Millers elastin stain (PSR-ME), and the result of the method of Example 1 is shown in FIG. 1. Tissue from the optimised protocol of Example 1 was also subjected to molecular analysis for the amount of DNA and GAG retention, the results of which are shown in FIGS. 2 and 3 respectively.

It can be seen from FIG. 1 that substantially no cellular material remains in the tissue decellularised by the inventive methods of Example 1. In addition FIGS. 2 and 3 shown that the quantity of DNA in samples T1 to T4 is substantially reduced compared to the control, while the concentration of GAGs crucial for tissue scaffold integrity is maintained.

Controls

The impact of various parameters was tested prior to achieving an optimised protocol. Experiments were initially carried out at various pressures (300-100 Mpa), once the optimised pressure of 150 MPa had been determined based on histological analysis of the tissue, the experiments were repeated at 31° C. and 35° C. Control experiments were performed by decellularising tissue without the decellularisation medium; wash buffer or SC—CO2. The pH was also monitored and showed a decrease to approx. 6.5. The resulting tissues show a lower amount of decellularisation and/or more damage to the tissue, compared to tissues prepared by the inventive method.

The above embodiments are described by way of example only. Many variations are possible without departing from the scope of the invention as defined in the appending claims.

The invention claimed is:

1. A method for decellularising a tissue comprising the steps of:
    a) adding a tissue to be decellularised to a decellularisation vessel;
    b) adding a decellularisation medium comprising at least one detergent and at least one enzyme selected from the group consisting of a deoxyribonuclease and a ribonuclease to the vessel;
    c) introducing supercritical carbon dioxide to the vessel with the tissue to be decellularised and the decellularisation medium present; and
    d) maintaining contact of the tissue with the supercritical carbon dioxide for a time sufficient to substantially decellularise the tissue.

2. The method of claim 1 wherein the detergent comprises sodium dodecyl sulphate, sodium deoxycholate, a detergent comprising hydrophilic polyoxyethylene-oxide and hydrophilic hydrocarbon moieties or any combination thereof.

3. The method of claim 2 wherein the detergent comprises a mixture of sodium dodecyl sulphate and sodium deoxycholate; a mixture of sodium dodecyl sulphate and a detergent comprising hydrophilic polyoxyethylene-oxide and hydrophilic hydrocarbon moieties; or a mixture of sodium deoxycholate and a detergent comprising hydrophilic polyoxyethylene-oxide and hydrophilic hydrocarbon moieties.

4. The method of claim 1 wherein the decellularisation medium further comprises an enzyme selected from the group consisting of a proteolytic enzyme, a lipase, a cellulase, and any combination thereof.

5. The method of claim 4 wherein the proteolytic enzyme comprises trypsin.

6. The method of claim 4 wherein the detergent of the decellularisation medium is selected from the group consisting of sodium dodecyl sulphate, sodium deoxycholate, a detergent comprising hydrophilic polyoxyethylene-oxide and hydrophilic hydrocarbon moieties, and combinations thereof.

7. The method of claim 6 wherein the detergent of the decellularisation medium comprises sodium dodecyl sulphate and/or sodium deoxycholate.

8. The method of claim 1 wherein the vessel is heated to at least 28° C.

9. The method of claim 1 wherein the supercritical carbon dioxide is maintained at a pressure of above 100 MPa.

10. The method of claim 1 wherein the tissue is maintained in contact with the supercritical carbon dioxide and decellularisation medium for a period of at least 24 hrs.

11. The method of claim 10 wherein the tissue is maintained in contact with the supercritical carbon dioxide and decellularisation medium for a period of at least 30 hrs.

12. The method of claim 1 further comprising a step e) of washing the decellularised tissue with a washing buffer.

13. The method of claim 12 wherein step e) comprises washing the decellularised tissue with phosphate buffered saline for a period of at least 24 hrs.

14. A method of manufacturing a tissue implant or scaffold comprising the steps of:
   a) adding a tissue to be decellularised to a decellularisation vessel;
   b) adding a decellularisation medium comprising at least one detergent and at least one enzyme selected from the group consisting of a deoxyribonuclease and a ribonuclease to the vessel;
   c) introducing supercritical carbon dioxide to the vessel with the tissue to be decellularised and the decellularisation medium present; and
   d) maintaining contact of the tissue with the supercritical carbon dioxide and the decellularisation medium for a time sufficient to substantially decellularise the tissue.

* * * * *